(12) United States Patent
Gorn et al.

(10) Patent No.: US 11,596,777 B2
(45) Date of Patent: Mar. 7, 2023

(54) CATHETER DEVICE INCLUDING A CONNECTOR

(71) Applicant: EM Device Lab, Inc., Austin, TX (US)

(72) Inventors: Michael Gorn, Austin, TX (US); Gary McGregor, Pflugerville, TX (US)

(73) Assignee: EM Device Lab, Inc., Austin, TX (US)

( * ) Notice: Subject to any disclaimer, the term of this patent is extended or adjusted under 35 U.S.C. 154(b) by 703 days.

(21) Appl. No.: 16/293,932

(22) Filed: Mar. 6, 2019

(65) Prior Publication Data

US 2020/0001057 A1 Jan. 2, 2020

Related U.S. Application Data

(63) Continuation-in-part of application No. 15/383,062, filed on Dec. 19, 2016, now Pat. No. 10,814,110.

(60) Provisional application No. 62/383,370, filed on Sep. 2, 2016, provisional application No. 62/292,782, filed on Feb. 8, 2016.

(51) Int. Cl.
*A61B 17/3209* (2006.01)
*A61M 27/00* (2006.01)
*A61M 3/02* (2006.01)

(52) U.S. Cl.
CPC ......... *A61M 27/00* (2013.01); *A61B 17/3209* (2013.01); *A61M 3/0279* (2013.01)

(58) Field of Classification Search
CPC .......... A61B 17/0487; A61B 17/06066; A61B 17/3415; A61B 2017/00292; A61B 2017/00473; A61B 2017/00641; A61B 2017/00876; A61B 2017/00946; A61B 2017/0461; A61B 2017/06071; A61B 2017/0608; A61B 2017/22067; A61B 2217/007; A61M 25/007; A61M 25/0097; A61M 27/00
See application file for complete search history.

(56) References Cited

U.S. PATENT DOCUMENTS

| 383,733 A | 5/1888 | Jenkins |
| 1,981,651 A | 11/1934 | Logan |
| 2,841,150 A | 7/1958 | Riall |
| 2,910,983 A | 11/1959 | James |

(Continued)

FOREIGN PATENT DOCUMENTS

| CA | 3038516 A1 | 8/2017 |
| EP | 3205368 | 8/2017 |

(Continued)

OTHER PUBLICATIONS

International Searching Authority, "Notification of Transmittal of the International Search Report and the Written Opinion of the International Searching Authority," dated Jun. 30, 2020, in International application No. PCT/US2020/021338.

(Continued)

*Primary Examiner* — Kai H Weng
(74) *Attorney, Agent, or Firm* — Trop, Pruner & Hu, P.C.

(57) ABSTRACT

In some embodiments, a catheter device may include a catheter including a proximal end and a distal end. The catheter device may further include a connector coupled to the proximal end of the catheter. The connector may include a base having a recess configured to receive the distal end of the catheter and may include a hinged portion configured to couple to the base to clamp the catheter within the recess.

13 Claims, 7 Drawing Sheets

(56) References Cited

U.S. PATENT DOCUMENTS

| | | | |
|---|---|---|---|
| 3,611,551 A | 10/1971 | Shave et al. | |
| 3,799,169 A | 3/1974 | Beroff | |
| 3,875,946 A | 4/1975 | Duncan | |
| 3,892,240 A | 7/1975 | Park | |
| 4,418,875 A | 12/1983 | Brine | |
| 4,524,771 A | 6/1985 | McGregor et al. | |
| 4,723,948 A | 2/1988 | Clark et al. | |
| 4,799,483 A | 1/1989 | Kraf | |
| 4,932,963 A | 6/1990 | Ritter et al. | |
| 5,002,528 A | 3/1991 | Palestrant | |
| 5,080,270 A | 1/1992 | Kai | |
| 5,089,011 A | 2/1992 | Korthoff | |
| 5,354,282 A | 10/1994 | Bierman | |
| 5,429,616 A * | 7/1995 | Schaffer | A61M 39/284 604/250 |
| 5,830,183 A * | 11/1998 | Krieger | A61M 25/02 604/96.01 |
| 6,290,691 B1 | 9/2001 | Krieger | |
| 6,893,424 B2 | 5/2005 | Shchervinsky | |
| 7,897,090 B2 | 3/2011 | Gudladt | |
| 8,079,991 B2 | 12/2011 | Watson | |
| 9,518,667 B2 | 12/2016 | Ramos et al. | |
| 2002/0004650 A1 | 1/2002 | Kuracina et al. | |
| 2003/0120216 A1 | 6/2003 | Bouphavichith et al. | |
| 2004/0006311 A1 | 1/2004 | Shchervinsky | |
| 2004/0243146 A1 | 12/2004 | Chesbrough et al. | |
| 2004/0245613 A1 | 12/2004 | Lee | |
| 2005/0240147 A1 | 10/2005 | Makower et al. | |
| 2007/0100296 A1 | 5/2007 | Hwang | |
| 2008/0116218 A1 | 5/2008 | Iacona | |
| 2008/0312578 A1* | 12/2008 | DeFonzo | A61M 39/284 604/6.16 |
| 2011/0125133 A1 | 5/2011 | Aggerholm et al. | |
| 2012/0245613 A1 | 9/2012 | Yee | |
| 2013/0274686 A1* | 10/2013 | Ziebol | A61M 39/20 604/265 |
| 2013/0274719 A1 | 10/2013 | Berkey et al. | |
| 2014/0060655 A1* | 3/2014 | Ramos | F16K 7/063 251/9 |
| 2014/0275777 A1 | 9/2014 | Gunday et al. | |
| 2014/0276655 A1 | 9/2014 | Murray et al. | |
| 2015/0141962 A1* | 5/2015 | Collins | A61M 25/02 604/513 |
| 2015/0250460 A1 | 9/2015 | Horeman et al. | |
| 2017/0224967 A1 | 8/2017 | Gorn et al. | |
| 2020/0001057 A1 | 1/2020 | Gorn et al. | |

FOREIGN PATENT DOCUMENTS

| | | |
|---|---|---|
| WO | 9966975 | 12/1999 |
| WO | WO 2008/021596 | 2/2008 |
| WO | WO 2010/062796 | 6/2010 |
| WO | WO2013059204 | 4/2013 |

OTHER PUBLICATIONS

Written Opinion and Search Report in PCT/US17/15571, dated May 18, 2017, 11 pages.

European Patent Office, Supplementary European Search Report dated Jun. 26, 2020 in European patent application No. EP 17 75 0568, 13 pages total.

Australian Patent Office, Australian Examination Report dated Feb. 6, 2020 in Australian patent application No. 2017218392, 4 pages total.

European Patent Office, Office Action dated Sep. 19, 2022 in European Patent Application No. 20766827.8 (6 pages).

Chinese Patent Office, Office Action dated Oct. 20, 2022 in Chinese Patent Application No. 202080019047.4 (12 pages).

United States Patent Office, Office Action dated Dec. 15, 2022 in U.S. Appl. No. 16/890,133 (9 pages).

* cited by examiner

CATHETER DEVICE INCLUDING A CONNECTOR

CROSS-REFERENCE TO RELATED APPLICATION(S)

The present application is a continuation-in-part of and claims priority to U.S. patent application Ser. No. 15/383,062 filed on Dec. 19, 2016 and entitled "Drainage Catheter System Including a Hub", which claims priority to and is a non-provisional of U.S. Provisional Patent Application No. 62/292,782 filed on Feb. 8, 2016 and entitled "Drainage Catheter Including a Hub" and claims priority to and is a non-provisional of U.S. Provisional Patent Application No. 62/383,370 filed on Sep. 2, 2016 and entitled "Drainage Catheter Including a Hub", each of which is incorporated herein by reference in its entirety.

FIELD

The present disclosure is generally related to catheter devices, and more particularly to catheter devices that include a connector and methods thereof. In some embodiments, the catheter devices may be configured to treat cutaneous and oral abscesses.

BACKGROUND

Surgical drains are used in a wide variety of different surgical procedures, for example, to drain fluid from a surgical area. Some examples where such drains are used may include plastic surgery, breast surgery (to prevent collection of blood, lymph fluid, or both), orthopedic procedures, chest drainage, infected cysts, pancreatic surgery (to drain secretions), biliary surgery, thyroid surgery, neurosurgery (to remediate risk of intracranial pressure), urinary catheters, nasogastric tubes, and other procedures.

One class of such surgical drains may be used on patients with cutaneous and oral abscesses, or collections of pus, hematomas, seromas or any other fluids requiring drainage. For example, abscesses can form anywhere in the body, from a superficial skin (subcutaneous) abscess to deep abscesses in muscle, organs, or body cavities. Treatment of such abscesses typically involves draining the accumulated fluid (such as pus) to resolve the infection or cause of the abscess and to facilitate recovery. One class of such surgical drains may require the patient or a care giver to adjust the drain to reopen clogged drainage paths to facilitate drainage.

The approach used to drain the accumulated fluid may depend on the size and location of the abscess. For subcutaneous abscesses, treatment typically includes creating an incision through the layers of the skin into the abscess cavity using a scalpel, expressing fluid (e.g., pus) from the abscess, and optionally using a hemostat to explore the wound and to break up pockets or localized areas of hardened pus. In some instances, packing material (such as a strip of gauze) may be inserted into the abscess cavity to prevent skin closure and re-accumulation of fluid in the abscess and to enable continued drainage. In other instances, a drainage catheter may be inserted through the incision and into the abscess to facilitate drainage and optionally irrigation of the abscess cavity.

The approach to draining abscesses in the oral cavity typically includes incision through the mucosa to the abscess cavity using a scalpel, expressing fluid (e.g., pus) from the abscess, and optionally using a hemostat to explore the wound and to break up pockets or localized areas of hardened pus. In most instances, a small drain is sutured into the cavity of the abscess cavity to mucosal closure and re-accumulation of fluid in the abscess and to enable continued drainage.

SUMMARY

In some embodiments, a drainage device may include a catheter including a proximal end and a distal end. The drainage device may further include a connector coupled to the proximal end of the catheter. The connector may include a body portion including a port sized to receive a tip of a syringe and including a lumen extending from the port to the proximal end of the catheter. The body portion may further include a hinged element configured to secure the distal end of the catheter against the body portion and to clamp the distal end of the catheter closed.

In some embodiments, a drainage device may include a catheter having a proximal end and a distal end and may include a connector coupled to the proximal end of the catheter and including a hinged fastener. The hinged fastener may be configured to close over a portion of the catheter near the distal end to form a loop and to clamp the distal end closed to prevent fluid flow through the distal end.

In some embodiments, a catheter device may include a catheter including a proximal end and a distal end. The catheter device may further include a connector coupled to the proximal end of the catheter. The connector may include a base having a recess configured to receive the distal end of the catheter and may include a hinged portion configured to couple to the base to clamp the catheter within the recess.

In other embodiments, a catheter device may include a catheter including a proximal end and a distal end and defining a lumen extending from the proximal end to the distal end. The catheter may include a plurality of openings extending from the lumen through a wall of the catheter. The catheter device may further include a connector coupled to the proximal end of the catheter. The connector may include a clamp configured to close over a portion of the catheter to compress the lumen to prevent fluid flow.

In still other embodiments, a catheter device may include a catheter including a proximal end and a distal end. The catheter may define a lumen extending from the proximal end to the distal end. The catheter device can further include a connector including a catheter-engagement element coupled to the proximal end. The connector may include a fluid port and may define a fluid passage extending from the fluid port to the lumen of the catheter through the catheter-engagement element. The connector may further include a base and a hinged element configured to couple to the base to clamp a portion of the catheter to compress the lumen to prevent fluid flow.

BRIEF DESCRIPTION OF THE DRAWINGS

In the following discussion, the same reference numbers are used in the various embodiments to indicate the same or similar elements.

DETAILED DESCRIPTION OF ILLUSTRATIVE EMBODIMENTS

Embodiments of devices and methods are described below that

Figure 1:
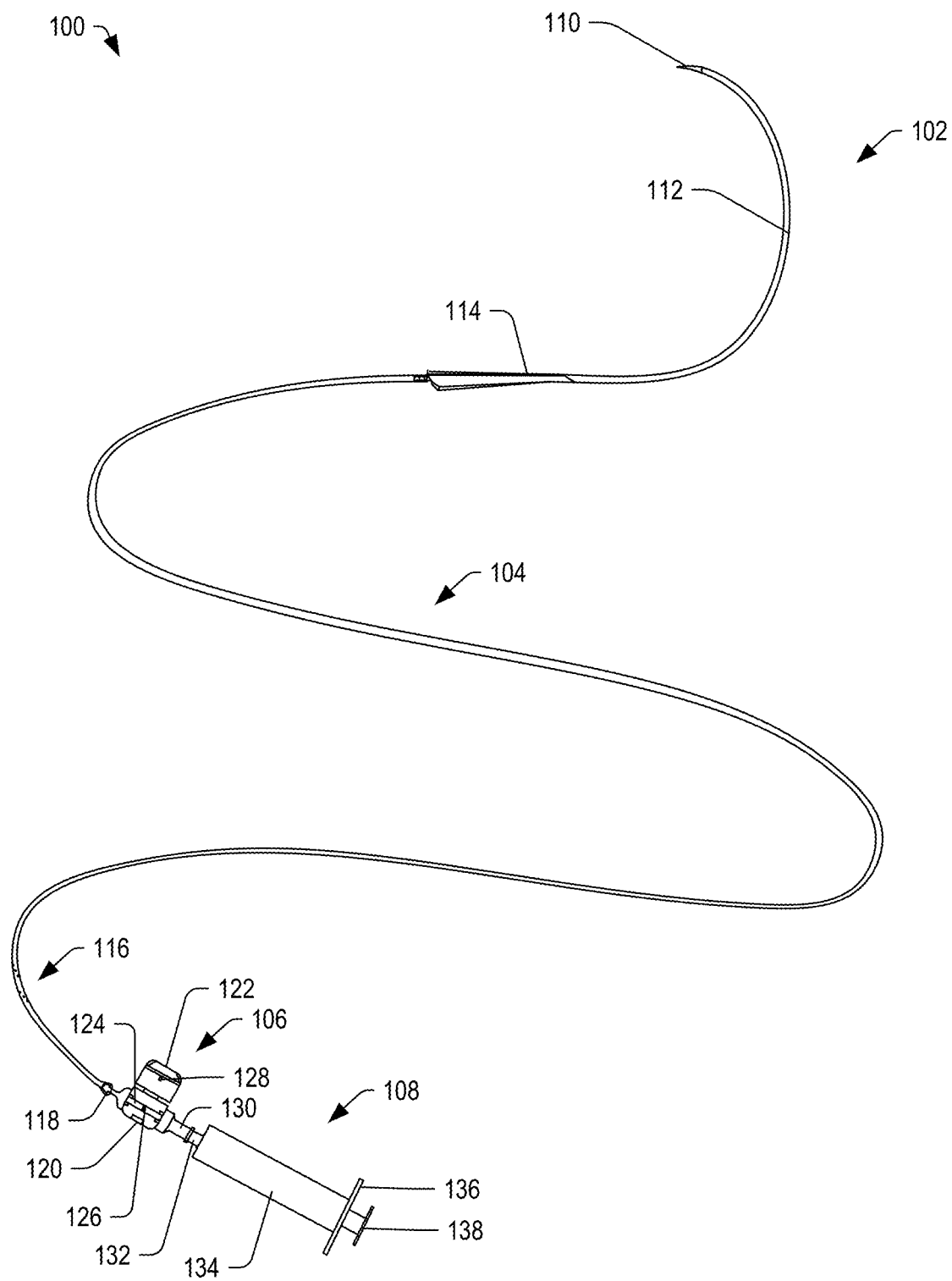
FIG. 1 depicts a diagram of a catheter device including a connector, in accordance with certain embodiments of the present disclosure.

FIG. 1 depicts a diagram of a catheter device 100 including a connector 106, in accordance with certain embodiments of the present disclosure. The catheter device 100 may include a needle 102, a catheter 104 coupled to the needle 102, and a connector 106 coupled to the catheter 104. In the illustrated example, the catheter 104 may define a lumen extending from a proximal end coupled to the needle 102 to a distal end coupled to the connector 106. The connector 106 may be releasably coupled to a syringe 108.

The needle 102 may include a point or tip 110 configured to puncture a surface or a plurality of layers, such as layers of skin. The needle 102 may further include a body portion 112 extending between the point 110 and a cutting blade 114. The body portion 112 may be curved according to a selected radius. The cutting blade 114 may be substantially triangle-shaped and may include a cutting edge along at least one side. In some embodiments, the point or tip 110 may puncture the surface and advance through underlying layers along a curved path defined by the curvature of the needle 102. The cutting blade 114 may trail the point or tip 110 along the curved path and the cutting edges of the cutting blade 114 may operate to widen the opening created by the point or tip 110. Further, trailing edges of the cutting blade 114 may be blunt or rounded such that reversing the direction of the force applied to the needle 102 may cause the blunt or rounded trailing edges to break up pockets or localized-areas of hardened pus.

The catheter 104 may include a long, flexible tube defining a lumen. The catheter 104 may be configured to allow fluid received from the connector 106 to flow through the lumen. Further, the catheter 104 may include a plurality of openings or holes, generally indicated at 116, which may be arranged in a spiral or helical pattern along a length of a portion of the catheter 104. The openings or holes 116 extend from the lumen within the catheter 104 through the exterior surface of the catheter 104 to allow fluid to flow from the lumen through the openings or holes 116.

The connector 106 may include a catheter-engagement element 118 configured to fit within the lumen of the catheter 104 and to secure the catheter 104 to the connector 106. The connector 106 may further include a base portion including clip 120 configured to engage and secure a hinged portion 122. The base portion may further include a recess or groove 124 sized to receive a distal end of the catheter 104. The recess or groove 124 may further include an opening or further recess 126 sized to receive a corresponding post 128 of the hinged portion 122. The connector 106 may also include a port 130 including an opening sized to receive a tip 132 of the syringe 108. The connector 106 may define a fluid passage extending from the fluid port 130 through the connector and to the lumen of the catheter 104 through the catheter-engagement element 118.

The syringe 108 may further include a barrel portion 134 coupled to the tip 132 and defining an enclosure. The barrel portion 134 may further include a flange 136. The syringe 108 may further include a plunger 138 sized to fit within the enclosure and configured to push fluid from the enclosure, through an opening in the tip 132, through the connector 106 and into the lumen of the catheter 104. Other embodiments are also possible.

In some embodiments, the needle 102 is inserted and pulled through one or more layers by a physician, drawing the catheter 104 through the layers. The physician may place a distal end of the catheter 104 into the recess 124 and may close the hinged portion 122, clamping the hinged portion 122 against the base portion and securing the post 128 within the recess 126 to close and seal the lumen of the catheter 104 between the post 128 of the hinged portion 120 and the opening or further recess 128 of the recess 124. By clamping down on the catheter 104, the lumen of the catheter 104 is closed off to fluid flow through the connector 106.

Figure 2:
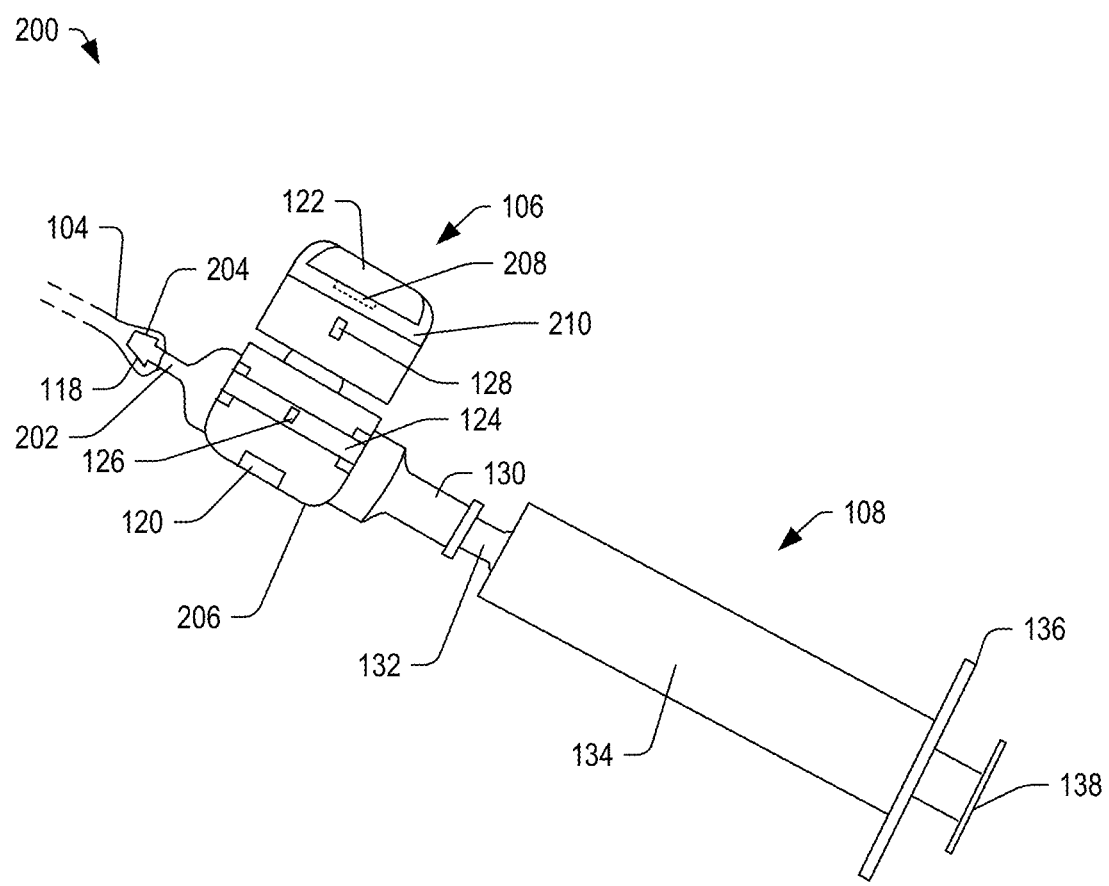
FIG. 2 depicts a portion of the catheter device of FIG. 1 including the connector coupled to a syringe, in accordance with certain embodiments of the present disclosure.

FIG. 2 depicts a portion 200 of the catheter device 100 of FIG. 1 including the connector 106 coupled to a syringe 108, in accordance with certain embodiments of the present disclosure. The connector 106 may include a catheter-engagement element 118 including a lumen configured to engage the lumen of the catheter 104. In this example, the catheter-engagement element 118 may include a polygonal shape including a neck portion 202 and a head portion 204. The distal end of the catheter 104 may stretch over the head portion 204 and tighten about the neck portion 202, securing the catheter 104 to the connector 106.

The connector 106 may further include a base portion 206, which defines a plurality of features configured to engage the hinged portion 122 and secure the catheter 104. The base portion 206 may include a latch or clip feature 120 configured to engage a corresponding feature or recess 208 formed beneath a reinforcing rib 210 on the hinged portion 122. The base portion 206 further includes the groove or recess 124 including an opening or notch 126 sized to receive the post 128 of the hinged portion 122. In operation, a portion of the catheter 104 may be placed into the groove or recess 124 and the hinged portion 122 may be closed, latching the hinged portion to the base portion 206 via the latch or clip feature 120 and the recess 208. Further, the post 128 may push into the notch 126 clamping the catheter 104 and compressing the lumen of the catheter 104 to close the catheter 104 to fluid flow.

Figure 3:
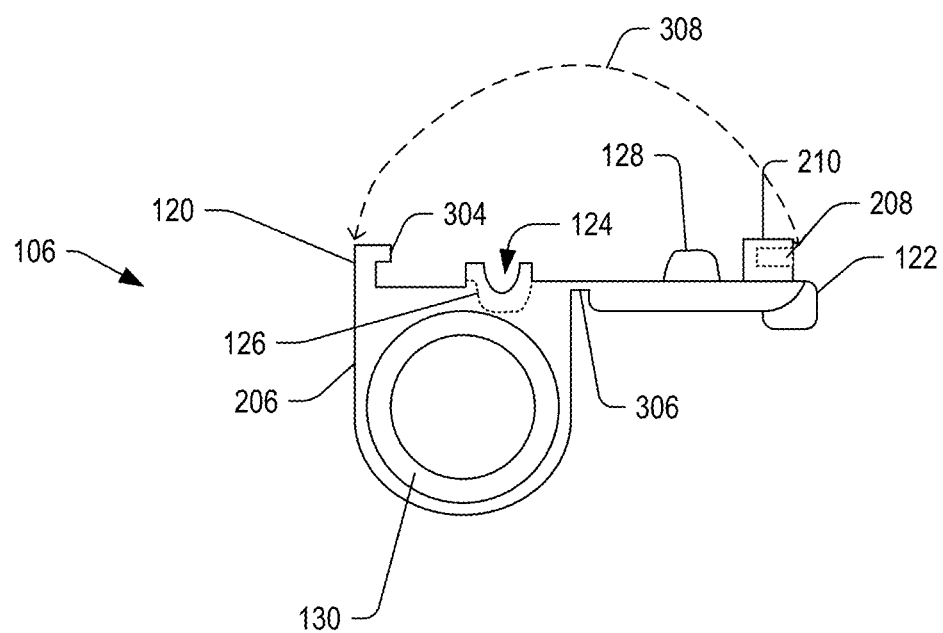
FIG. 3 depicts a side view of the connector, in accordance with certain embodiments of the present disclosure.

FIG. 3 depicts a side view 300 of the connector 106, in accordance with certain embodiments of the present disclosure. The connector 106 includes the port 130 to receive the tip of the syringe. Further, the connector 106 includes the base 206 coupled to a hinged portion 122 by a hinge 306. The base 206 includes a clip 120 including an extension 304 configured to engage a recess 208 in a reinforcing rib 210. Further, the hinged portion 122 includes a post 128 configured to fit within the opening or notch 126.

As shown in the illustrated example, the hinged portion 122 opens and closes along a path indicated by the dashed arrow 308. The extension 304 of the clip 120 may snap into the recess 208. Further, the post 128 may extend into the recess 124 and into the opening or notch 126 to clamp the catheter 104 within the recess 124. Other embodiments are also possible.

Figure 4:
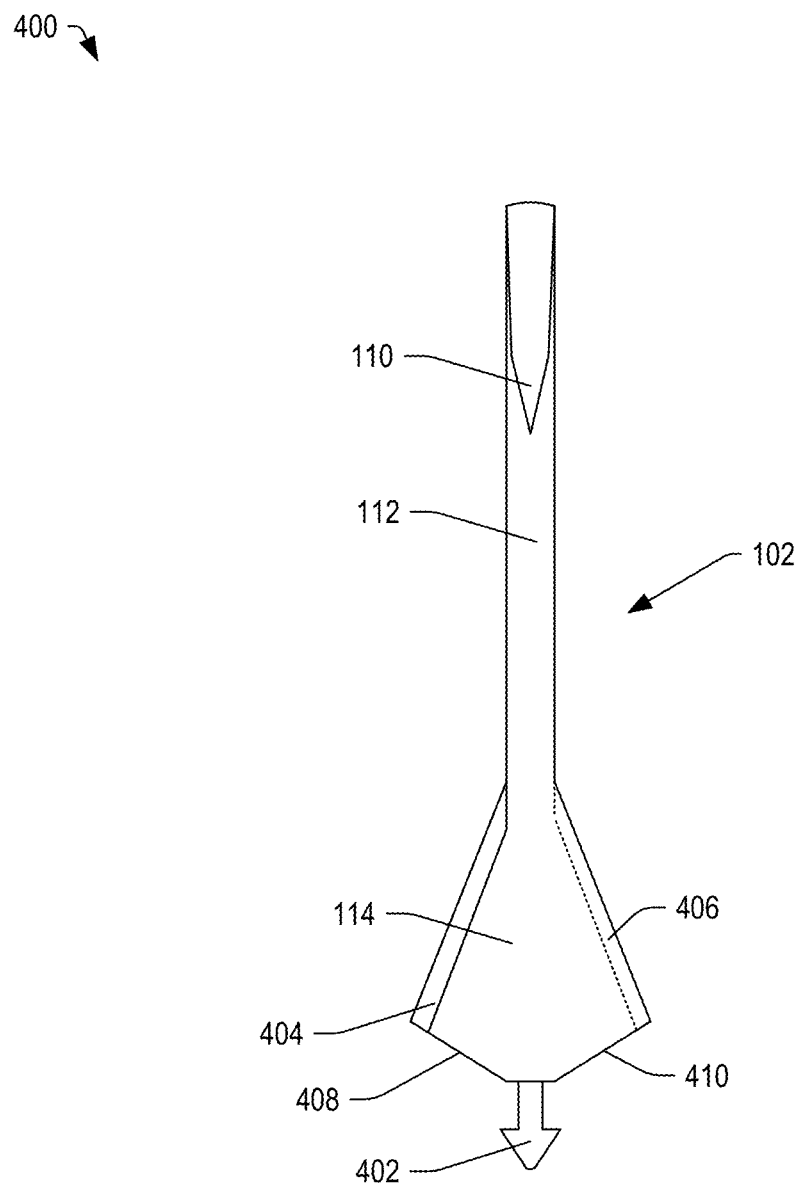
FIG. 4 depicts a top view of a needle of the catheter device of FIG. 1, in accordance with certain embodiments of the present disclosure.

FIG. 4 depicts a top view 400 of the needle 102 of the catheter device 100 of FIG. 1, in accordance with certain embodiments of the present disclosure. The needle 102 includes the tip 110, the body portion 112, and the cutting blade 114. In this example, the cutting blade 114 may be substantially planar, while the tip 110 and the body portion 112 may define a curvature. The cutting blade 114 may extend outward from the body portion 112, forming wings or edges 404 and 406, which may be sharpened to facilitate widening of the opening formed by the tip 110 and the body 112 of the needle 102. In this example, one side of each of the edges 404 and 406 is sharpened. Trailing edges 408 and 410 may be blunted or rounded. The practitioner may manipulate the needle 102 to use the trailing edges to break up pockets within an abscess, for example.

A catheter-coupling element 402 may extend from an end of the needle 102 adjacent to the trailing edges 408 and 410. The element 402 may include an arrow-shaped or other-shaped feature 402 that can be pushed into the lumen of the catheter 104, such that the catheter 104 expands around the arrowhead of the element 402 and narrows to secure the catheter 104 to the needle 102.

Figure 5:
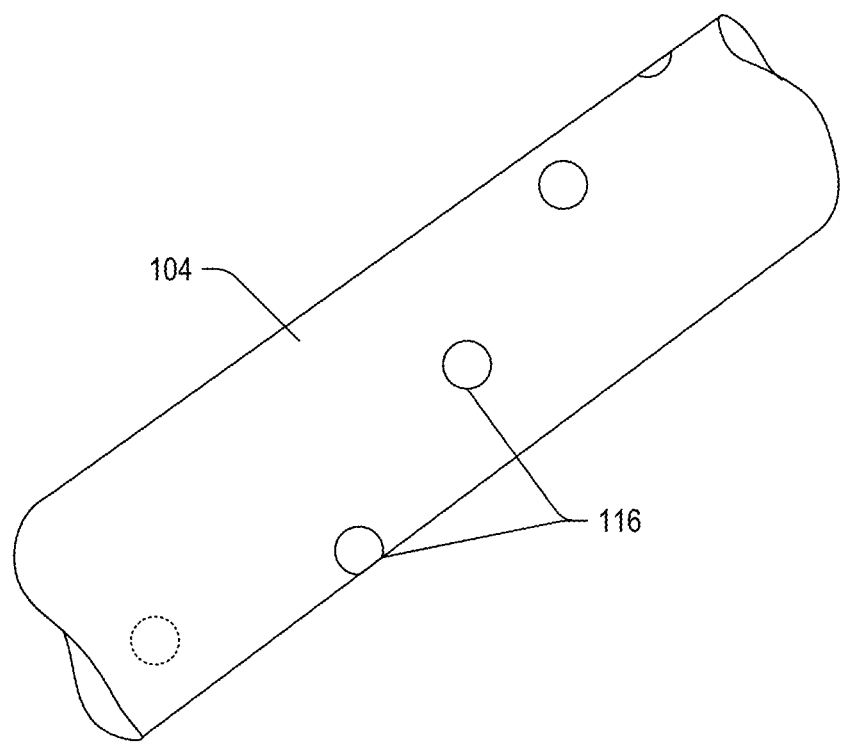
FIG. 5 depicts a portion of the catheter including a helical arrangement of openings, in accordance with certain embodiments of the present disclosure.

FIG. 5 depicts a portion 500 of the catheter 104 including a helical arrangement of openings 116, in accordance with certain embodiments of the present disclosure. As shown, openings 116 are provided in the catheter 104, which openings 116 extend from the lumen through the wall of the catheter 104 to provide drainage holes through which saline, antibiotics, other fluids, or any combination thereof may be delivered. In an example, the openings 116 may be positioned within an abscess by a practitioner, and the practitioner may press the plunger of a syringe coupled to the connector 106 to deliver fluid to the abscess via the lumen of the catheter 106 and through the openings 116.

In some embodiments, the arrangement of openings 116 may be helical, which allows for a substantially even distribution of fluid from the catheter 104, even if the catheter 104 is twisted. Other embodiments are also possible.

Figure 6:
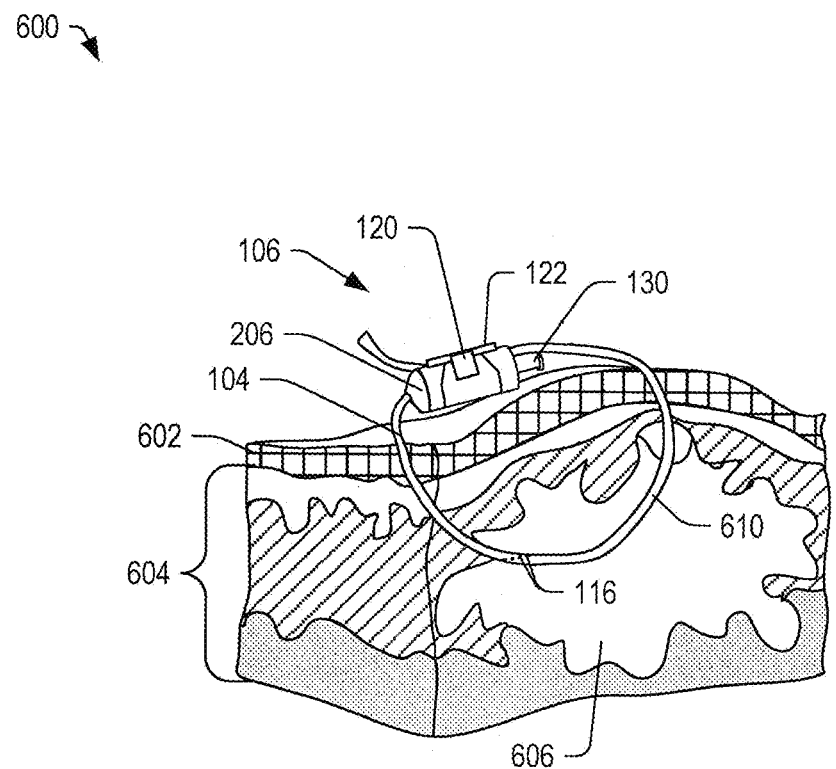
FIG. 6 depicts a diagram of an embodiment of the catheter device configured to drain an abscess, in accordance with certain embodiments of the present disclosure.

FIG. 6 depicts a diagram 600 of an embodiment of the catheter device 100 of FIG. 1 configured to drain an abscess, in accordance with certain embodiments of the present disclosure. The catheter device 106 includes a base 206 including a clip 120 configured to couple to the hinged portion 122 to clamp the distal end of the catheter 104 after the catheter 104 has been drawn into position within the abscess 606 by the needle 102. The catheter device 106 is coupled to a proximal end of the catheter 104 and is configured to provide a fluid conduit from a port 130 sized to receive the tip of a syringe to a lumen of the catheter 104. The base 206 and the hinged portion 122 may cooperate to clamp the distal end of the catheter 104.

In this example, the catheter 610 may extend through a first incision through the epidermis 602 and optionally through one or more layers of the dermis 604, through an abscess 606, and out from a second incision. The connector 106 includes the fluid port 130 to receive a sterile irrigation fluid, such as saline, medication, sterilized water, other fluids, or any combination thereof. The catheter 104 includes a lumen coupled to the irrigation port 130 and coupled to openings 116, which are positioned within the abscess 606, to deliver irrigation fluid into the abscess 606.

In the illustrated embodiment of FIG. 6, the catheter 104 and the connector 106 cooperate to facilitate the introduction of irrigation fluid via the irrigation port 130 and the openings 116. The connector 106 secures both ends of the catheter 104 to provide a secure loop that prevents the catheter 104 from being pulled out of the abscess. Further, the connector 106 prevents fluid flow through the portion of the catheter 104 that is clamped within the connector 106, making it possible to push irrigation fluid through a port in the connector 104 and through openings 116 into the abscess so that the fluid does not flow out the other end of the catheter 104. Other embodiments are also possible.

Figure 7:
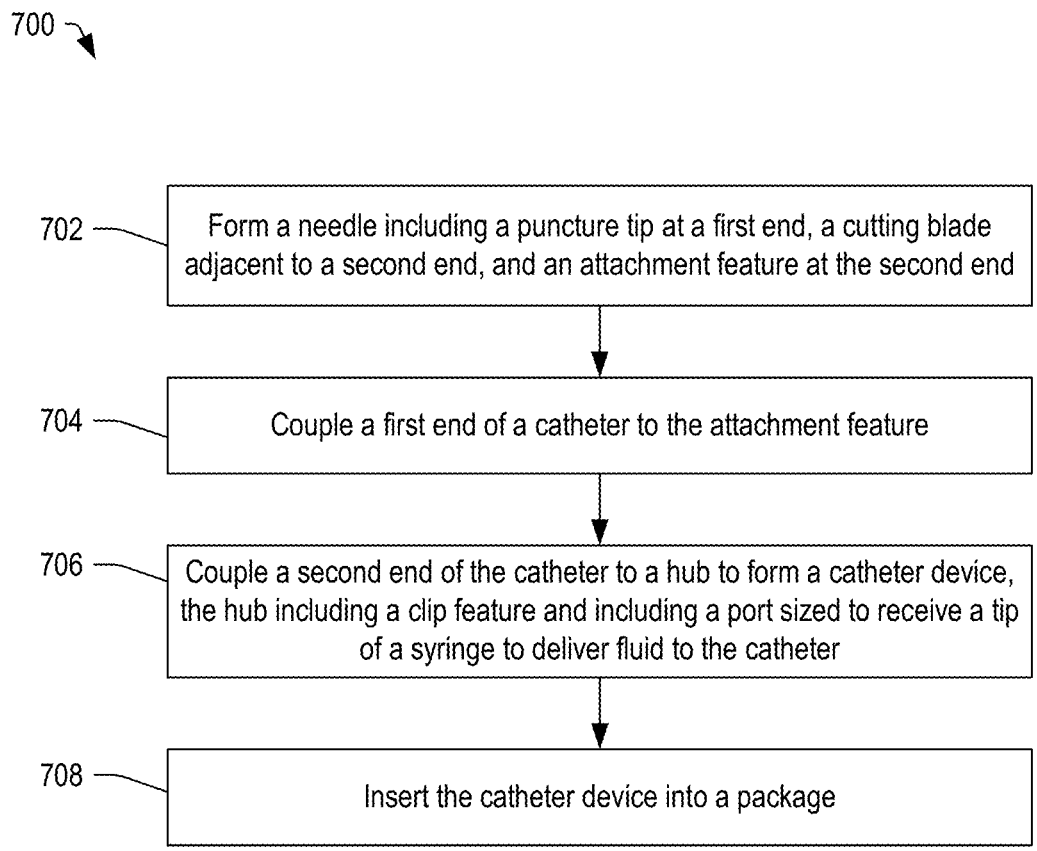
FIG. 7 depicts a flow diagram of a method of producing a catheter device, in accordance with certain embodiments of the present disclosure.

FIG. 7 depicts a flow diagram of a method 700 of producing a catheter device, in accordance with certain embodiments of the present disclosure. At 702, the method 700 can include forming a needle including a puncture tip at a first end, a cutting blade adjacent to a second end, and an attachment feature at the second end. Between the puncture tip and the cutting blade, the needle may include a curved body portion.

At 704, the method 700 can include coupling a first end of the catheter to the attachment feature. In some embodiments, the attachment feature may include a narrow portion and bulbous or wider portion. The attachment feature may be pressed into the lumen of the catheter, and the catheter may stretch to accommodate the bulbous or wider portion and may retract about the narrow portion to couple the catheter to the needle.

At 706, the method 700 can include coupling a second end of the catheter to a hub to form a catheter device, where the hub includes a clip feature and a port sized to receive a tip of a syringe to deliver fluid to the catheter. The catheter may fit over a catheter-engagement element, which may couple the catheter to the connector.

At 708, the method 700 may include inserting the catheter device into a package. The package may be a cardboard packaging including openings and securing features configured to secure the catheter device within the packaging. Other embodiments are also possible.

In conjunction with the devices described above with respect to FIGS. 1-7, a catheter device is disclosed that includes a needle, a catheter including a distal end coupled to the needle and including a proximal end, and a connector coupled to the proximal end. The connector may include a port sized to receive a tip of a syringe and may include a catheter-coupling element configured to couple the port to the lumen of the catheter to allow fluid to flow from the port into the lumen. The connector may further r include a base including a clip and a hinged element including a recess configured to engage the clip to clamp the hinged element to the base. The base may further include a recess configured to receive a distal portion of the catheter, and the hinged element may clamp the distal portion of the catheter to the base. Further, the hinged portion may include a post configured to compress the catheter to block fluid flow.

It should be appreciated that the catheter device described above may be used in a variety of contexts including but not limited to plastic surgery, breast surgery (to prevent collection of blood. lymph fluid, or both), orthopedic procedures, chest drainage, infected cysts, pancreatic surgery (to drain secretions), biliary surgery, thyroid surgery, neurosurgery (to remediate risk of intracranial pressure), urinary catheters, nasogastric tubes, and other procedures. In some embodiments, such as oral surgery, the size of the catheter device may be implemented with a smaller size in order to reduce irritation. In other embodiments, the hub may be larger in order to facilitate access to fluid ports. Other embodiments are also possible.

Although the present invention has been described with reference to preferred embodiments, workers skilled in the art will recognize that changes may be made in form and detail without departing from the scope of the invention.

What is claimed is:
1. A device comprising:

a catheter including a proximal end and a distal end and defining a lumen extending from the proximal end to the distal end, the catheter including a plurality of openings extending from the lumen through a wall of the catheter;

a needle including a connection element configured to couple the needle to the distal end of the catheter; and a connector coupled to the proximal end of the catheter and including a clamp configured to close over a portion of the catheter to compress the lumen to prevent fluid flow;

wherein: (a) the needle includes a tip, a cutting blade, and a body portion extending between the tip and the cutting blade; (b) the cutting blade comprises first and second sharpened edges that extend outward and away from the body portion; (c) the first and second sharpened edges taper outwardly away from the body portion as the first and second sharpened edges extend proximally and away from the tip; and (d) at least a portion of the connection element is included within a distal portion of the lumen.

2. The device of claim 1, wherein the clamp includes a base portion including a recess configured to receive the portion of the catheter.

3. The device of claim 2, further comprising:
a hinged portion coupled to the base portion by a hinge, the hinged portion including a support defining an additional recess; and
wherein the base portion further includes a clip configured to engage the additional recess to secure the hinged portion to the base portion in a closed state.

4. The device of claim 3, further including a post extending from the hinged portion and configured to extend into the recess to compress the lumen when the hinged portion is closed over the catheter.

5. The device of claim 1, wherein the connector further includes a fluid port configured to receive a tip of a syringe, the connector defining a fluid passage extending from the fluid port to the lumen of the catheter.

6. The device of claim 1, wherein the plurality of openings are closer to the proximal end than to the distal end of the catheter.

7. The device of claim 1, wherein the body portion is curved to form an arcuate shape.

8. The device of claim 7, wherein the cutting blade is substantially planar.

9. The device of claim 8, wherein:
the first sharpened edge is sharpened on a first side of the cutting blade but not a second side of the cutting blade;
the second sharpened edge is sharpened on the second side of the cutting blade but not the first side of the cutting blade.

10. The device of claim 9, wherein:
the first sharpened edge is coupled to a first blunted edge, the first blunted edge being proximal to the first sharpened edge;
the second sharpened edge is coupled to a second blunted edge, the second blunted edge being proximal to the second sharpened edge.

11. The device of claim 10, wherein the connection element extends proximal to the first and second blunted edges.

12. The device of claim 11, wherein the tip, the cutting blade, the body portion, and the connection element are all monolithic with one another.

13. The device of claim 12, wherein:
the distal portion of the lumen is stretched around the portion of the connection element;
an additional portion of the lumen, which is proximal to the stretched distal portion of the lumen, is relaxed and unstretched.

\* \* \* \* \*